United States Patent
Westermayer et al.

(10) Patent No.: US 8,258,336 B2
(45) Date of Patent: Sep. 4, 2012

(54) PROCESS FOR PREPARING UNSATURATED CARBOXYLIC ESTERS

(75) Inventors: Heribert Westermayer, Burghausen (DE); Johann Wagner, Burghausen (DE); Willibald Dafinger, Röhrnbach (DE); Peter Holl, Emmerting (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 12/989,018

(22) PCT Filed: Apr. 21, 2009

(86) PCT No.: PCT/EP2009/054728
§ 371 (c)(1),
(2), (4) Date: Oct. 21, 2010

(87) PCT Pub. No.: WO2009/130211
PCT Pub. Date: Oct. 29, 2009

(65) Prior Publication Data
US 2011/0054210 A1     Mar. 3, 2011

(30) Foreign Application Priority Data
Apr. 24, 2008 (DE) .......................... 10 2008 001 366

(51) Int. Cl.
*C07C 67/05* (2006.01)
(52) U.S. Cl. ...................................................... 560/245
(58) Field of Classification Search .................. None
See application file for complete search history.

(56) References Cited

U.S. PATENT DOCUMENTS

| | | | |
|---|---|---|---|
| 3,840,590 A * | 10/1974 | Fisher et al. | ................... 560/245 |
| 6,420,595 B1 | 7/2002 | Hallinan et al. | |
| 7,202,377 B2 | 4/2007 | Rinne et al. | |
| 2006/0094896 A1 | 5/2006 | Rinne et al. | |

FOREIGN PATENT DOCUMENTS

| | | | |
|---|---|---|---|
| DE | 2359286 A | 6/1975 | |
| EP | 1655279 A | 5/2006 | |
| GB | 1401106 | * 11/1976 | |

OTHER PUBLICATIONS

Van Bergen, Mark, International Search Report mailed Sep. 7, 2009, 2 pgs.

* cited by examiner

*Primary Examiner* — Paul A Zucker
(74) *Attorney, Agent, or Firm* — RatnerPrestia

(57) ABSTRACT

A process for preparing unsaturated carboxylic esters includes reaction of alkenes having 2 to 6 carbon atoms with alkanecarboxylic acids having 1 to 6 carbon atoms in the presence of an oxygenous gas and in the presence of a heterogeneous noble metal catalyst by means of a continuous homogeneous gas phase process in a reactor. A gaseous phase (cycle gas) is circulated, and the cycle gas is laden with alkanecarboxylic acid in an acid saturator before entry into the reactor. In a presaturator connected upstream of the acid saturator, the cycle gas is laden with a portion of the amount of alkanecarboxylic acid used for saturation, and then it is transferred to the acid saturator and laden there with the remaining amount of alkanecarboxylic acid.

7 Claims, 1 Drawing Sheet

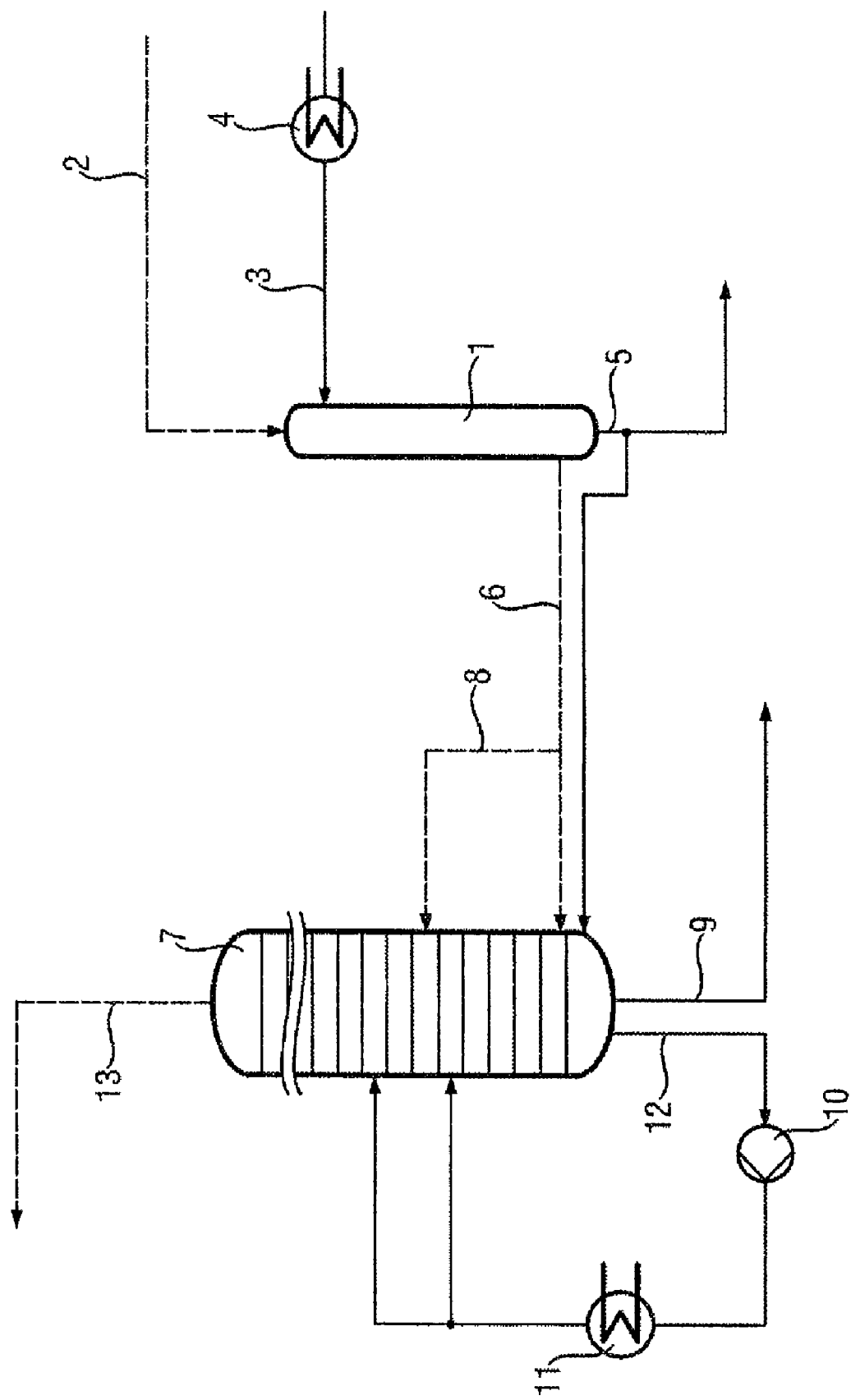

PROCESS FOR PREPARING UNSATURATED CARBOXYLIC ESTERS

CROSS REFERENCE TO RELATED APPLICATIONS

This application is the national stage filing of PCT application number EP2009/054728, filed Apr. 21, 2009, and claims priority of German patent application number 102008001366.8, filed Apr. 24, 2008, the entireties of which applications are incorporated herein by reference.

FIELD OF THE INVENTION

The invention relates to a process for preparing unsaturated carboxylic esters by means of reaction of alkenes having 2 to 6 carbon atoms with alkanecarboxylic acids having 1 to 6 carbon atoms, in the presence of an oxygenous gas, by means of a continuous homogeneous gas phase process, and in the presence of a heterogeneous noble metal catalyst.

BACKGROUND OF THE INVENTION

The preparation of unsaturated carboxylic esters by means of reaction of alkenes having 2 to 6 carbon atoms with alkanecarboxylic acids having 1 to 6 carbon atoms, in the presence of an oxygenous gas, by means of a continuous homogeneous gas phase process, and in the presence of a heterogeneous noble metal catalyst, is already known. Of particular significance is the preparation of vinyl acetate by a reaction of ethylene with acetic acid and oxygen or oxygenous gases over fixed bed catalysts in the gas phase.

The reactions are effected generally at pressures of 1 to 50 bar, preferably 5 to 15 bar, and at temperatures of 50 to 250° C., preferably 130 to 200° C. Suitable catalysts contain a noble metal component and an activator component. The noble metal component consists generally of palladium and/or compounds thereof. Frequently, gold and/or rhodium or compounds thereof are additionally present. The activator component consists of compounds of elements of main group 1 and/or 2 and/or cadmium. It is also possible for rhenium and/or zirconium compounds to be present. These components are generally applied to support materials, for example silica, aluminium silicates, titanium oxide, zirconium oxide, silicon carbide or aluminium oxide.

The mixture used for the reaction (olefin, alkene, oxygen) generally contains a multiple molar excess of olefin. The ethylene conversion is therefore incomplete in the reaction, and the unconverted olefin must be recycled to the reaction in a circulation system. This recycled olefin-containing gas is referred to as cycle gas. In a saturator connected upstream of the reactor (in vinyl acetate preparation: acetic acid saturator), the olefin-containing cycle gas (in vinyl acetate preparation: ethylene-containing cycle gas) is loaded with the appropriate carboxylic acid (in vinyl acetate preparation: acetic acid) and then loaded with oxygen.

Subsequently, the reaction mixture is passed into the reactor. The hot reaction mixture which leaves the reactor and, in the case of vinyl acetate preparation, consists essentially of unconverted ethylene, unconverted acetic acid, unconverted oxygen, vinyl acetate, water of reaction, carbon dioxide, and inerts introduced with the oxygen and ethylene (for example nitrogen, ethane, methane and argon) is cooled, optionally with upstream connection of a dewatering column. This condenses the majority of the acetic acid, and a portion of the vinyl acetate and of the water. The condensate is separated in subsequent steps, the constituents thereof are isolated and the acetic acid (returned acetic acid) is recycled into the process. The uncondensed residual gas contains principally ethylene, $CO_2$ and inerts and, after $CO_2$ scrubbing and inerts removal, is conducted as cycle gas into the acetic acid saturator.

However, the loading of cycle gas with acetic acid in the acetic acid saturator has the disadvantage that the acetic acid saturator becomes fouled even after short run times. The saturator is generally a column in which dry cycle gas (without acetic acid and water) is first conducted directly into the column from the bottom upward, and acetic acid is metered in. In the lower column region in particular, there is fouling at the introduction site of the dry and hot cycle gas, which impairs the production capacity and even triggers a production shutdown for cleaning.

U.S. Pat. No. 6,420,595 B1 discloses equipping the saturator with a distillation column, withdrawing the fouling with the column bottoms, and removing the impurities from the acetic acid under reduced pressure in an acid recovery unit (ARU), and recycling these impurities into the saturator.

U.S. Pat. No. 7,202,377 B1 ascribes the formation of fouling in the acetic acid saturator to the proportion of returned acetic acid which has been obtained from the condensed proportion of the reaction mixture and which is used in addition to fresh acetic acid to saturate the cycle gas. It is advisable to clean the cycle gas by means of a rectification section attached to the saturation column and to divide the liquid effluxing from the bottom of the saturation column into two substreams, one substream being recycled without workup, and the other substream, after removal of high boilers and polymers, being recycled into a high-temperature thin-film evaporator.

SUMMARY OF THE INVENTION

It was an object of the present invention to provide a process for preparing unsaturated carboxylic esters, in which the formation of fouling in the acid saturator connected upstream of the reactor is suppressed so effectively that the laborious cleaning known from the prior art can be avoided.

It has been found that, surprisingly, a presaturation of the cycle gas, preferably with returned acetic acid, in an upstream presaturator can drastically reduce the fouling in the acid saturator.

BRIEF DESCRIPTION OF THE DRAWING

FIG. 1 is a schematic drawing of equipment and process steps suitable for saturating and presaturating an alkene-containing recycle gas with an alkanecarboxylic acid according to the invention.

DETAILED DESCRIPTION OF THE INVENTION

The invention provides a process for preparing unsaturated carboxylic esters by means of reaction of alkenes having 2 to 6 carbon atoms with alkanecarboxylic acids having 1 to 6 carbon atoms, in the presence of an oxygenous gas and in the presence of a heterogeneous noble metal catalyst, by means of a continuous homogeneous gas phase process in a reactor, by circulating a gaseous phase (cycle gas) and loading the cycle gas with alkanecarboxylic acid in an acid saturator before entry into the reactor, characterized in that upstream of the acid saturator is connected a presaturator in which the cycle gas is loaded with a portion of the amount of alkanecarboxylic acid used for saturation, then is transferred into the acid saturator and loaded there with the remaining amount of alkanecarboxylic acid.

The invention is described using the example of vinyl acetate preparation, though the process can generally be used to prepare unsaturated carboxylic esters. The description should therefore be understood such that it is generally possible to use alkenes having 2 to 6 carbon atoms in the process described hereinafter, and it is also possible to use other alkanecarboxylic acids having 1 to 6 carbon atoms instead of acetic acid.

Suitable presaturators, and also saturators, are gas-liquid contact apparatus in generally, for example columns with grid packings, columns with random packings, columns with trays or other internals, and Venturi scrubbers, and in the simplest case a pipeline. For the presaturator, preference is given to internal-free quenches or scrubbers, for example spray, jet or Venturi scrubbers.

The cycle gas is preferably introduced into the presaturator from the top. It can also be supplied from the bottom in countercurrent to the acetic acid supplied. It is preferably conducted in cocurrent with the acetic acid. In a preferred embodiment, radially homogeneously arranged nozzles in a plane at right angles to the vertical axis are used in the saturator, through which the acetic acid is sprayed into the presaturator. The acetic acid is preferably sprayed in from the top.

The ethylene-containing cycle gas generally enters the presaturator with a temperature of 100 to 170° C., preferably at 120 to 150° C. Depending on the pressure level of the process, the acetic acid is introduced into the presaturator at a temperature of 90 to 200° C., preferably at 100 to 150° C. The acetic acid evaporates on contact with the cycle gas and the cycle gas is cooled. The acetic acid is preferably introduced in such a quantitative ratio that it does not evaporate completely. The presaturation is preferably regulated such that at least 5% by weight, more preferably with 25 to 75% by weight, of the acetic acid supplied in the presaturation is obtained as a liquid in the presaturator.

For the presaturation, preferably 20 to 80% by weight, more preferably 50 to 80% by weight, of the acetic aid, based on the total amount of acetic acid which is added in presaturator and saturator, is added to the ethylene-containing cycle gas. The remaining amount is used to load the cycle gas in the saturator. For the presaturation, acetic acid from any process steps can be used, for example returned acetic acid which has been recovered from the reaction mixture leaving the reactor, or returned acetic acid from the workup of acetic acid obtained in liquid form in the process (residue workup), fresh acetic acid or acetic acid from the pumparound of the saturator. In a preferred embodiment, the procedure is that the returned acetic acid which has been recovered from the reaction mixture leaving the reactor is used for presaturation, preferably predominantly, i.e. >50% by weight, or exclusively.

The proportion of liquid acetic acid obtained in the presaturator is drawn off from the presaturator. The liquid proportion from the presaturator is preferably passed completely or partially into the bottom of the acetic acid saturator. The liquid proportion from the presaturator can also be conducted completely or partially directly into the acetic acid workup.

The acetic acid saturator is preferably designed as a column; for example as a column with random packing or preferably as a tray column with a number of rectifying trays.

In the process according to the invention, the presaturated cycle gas from the presaturator is transferred to the acetic acid saturator. The temperature level is now preferably 80 to 140° C. In the saturator, the cycle gas is loaded with the remaining amount of acetic acid. Preference is given to using fresh acetic acid for this purpose. It is also possible to use fresh acetic acid in any combination with the liquid acetic acid component from the presaturator and/or returned acetic acid which has been recovered from the reaction mixture leaving the reactor and/or the residue workup. The ethylene-containing cycle gas stream partially saturated with acetic acid is preferably fed in the lower quarter, more preferably below the lowermost tray and above the liquid level, of the acetic acid saturator. In a further embodiment, a substream, preferably up to 40% by volume, can be withdrawn from this ethylene-containing cycle gas laden with acetic acid from the presaturator, before entry into the acetic acid saturator, and this substream can be introduced into the acetic acid saturator above the feed of the main stream, effectively as a bypass.

At the bottom of the acetic acid saturator, bottom product can be withdrawn. In a preferred embodiment, bottom product is withdrawn at the bottom of the acetic acid saturator, heated up and recycled into the acetic acid saturator. In a preferred embodiment, this recycling can be distributed between several trays. By virtue of this so-called pumparound, the temperature in the acetic acid saturator and hence the loading of the cycle gas with acetic acid can be regulated. In the case of a pumparound, the above-described bypass is introduced above the lowermost feed of the pumparound into the acetic acid saturator.

After the loading with acetic acid and the loading with ethylene and oxygen, the cycle gas is transferred into the reactor.

FIG. 1 shows, by way of example, a schematic embodiment of the process according to the invention:

Ethylene-containing cycle gas is fed into a presaturator 1 in the upper third via line 2, and, in cocurrent, acetic acid preheated with a heating device 4 via line 3. Liquid bottom product can be withdrawn from the presaturator via line 5 and conducted completely or partially to the acetic acid saturator 7 or to the residue workup. The acetic acid-laden, ethylene-containing cycle gas is withdrawn in the lower third of the presaturator via line 6 and transferred into the acetic acid saturator 7, preferably in the lower third thereof.

In the preferred embodiment, a substream is withdrawn via line 8 from the ethylene-containing, acetic acid-laden cycle gas before entry into the acetic acid saturator, and this substream is introduced into the acetic acid saturator 7 above the lowermost feed of line 6.

Liquid bottom product can be withdrawn from the acetic acid saturator 7 via line 9. After heating in the acetic acid saturator 7, bottom product can be recycled (pumparound) through the line 12 equipped with pump 10 and heating device 11.

The acetic acid-saturated cycle gas leaves the acetic acid saturator via line 13.

In a mode of operation without a presaturator, in a plant for producing vinyl acetate on the industrial scale (approx. 200,000 jato of VAc), the pumped circulation rates and then later also the cycle gas rate had to be reduced as early as after 2 to 3 months, owing to rising pressure drops and flooding phenomena in the column, which were attributable to the fouling of the acetic acid saturator. Problems occurred in the liquid efflux in the column, which lead to level variations in the bottoms and in extreme cases to the bottom stream running dry. In the advanced state, production declined and ultimately cleaning shutdowns with a production outage had to be carried out at 3- to 9-month intervals.

As a result of the incorporation of the acetic acid presaturator, the cleaning cycles were prolonged to 2 to 3 times the time interval.

The invention claimed is:

1. A process for preparing an unsaturated carboxylic ester, comprising reaction of an alkene having 2 to 6 carbon atoms with an alkanecarboxylic acid having 1 to 6 carbon atoms, in the presence of an oxygenous gas and in the presence of a heterogeneous noble metal catalyst, by means of a continuous homogeneous gas phase process in a reactor, wherein the method comprises circulating a cycle gas comprising the alkene and loading the cycle gas with a quantity of said alkanecarboxylic acid in an acid saturator before entry into the reactor, wherein upstream of the acid saturator is connected a presaturator in which the cycle gas is loaded with another quantity of the alkanecarboxylic acid and then is transferred into the acid saturator, wherein predominantly alkanecarboxylic acid which has been recovered from the reaction mixture leaving the reactor is used for presaturation, and wherein the presaturation is regulated such that at least 5% by weight of the alkanecarboxylic acid supplied to the presaturator is not evaporated in the presaturator and issues as a liquid from it.

2. The process according to claim 1, wherein 20 to 80% by weight of the total amount of alkanecarboxylic acid which is added in the presaturator and the acid saturator, is added in the presaturator.

3. The process according to claim 1, wherein the cycle gas enters the presaturator at a temperature of 100 to 170° C. and the alkanecarboxylic acid enters the presaturator with a temperature of 90 to 200° C.

4. The process according to claim 1, wherein the alkanecarboxylic acid loaded in the acid saturator is fresh alkanecarboxylic acid, optionally in any combination with liquid alkanecarboxylic acid exiting the presaturator and/or returned alkanecarboxylic acid which has been recovered from the reaction mixture leaving the reactor and/or from process residue work-up.

5. A process for preparing an unsaturated carboxylic ester, comprising reaction of an alkene having 2 to 6 carbon atoms with an alkanecarboxylic acid having 1 to 6 carbon atoms, in the presence of an oxygenous gas and in the presence of a heterogeneous noble metal catalyst, by means of a continuous homogeneous gas phase process in a reactor, wherein the method comprises circulating a cycle gas comprising the alkene and loading the cycle gas with a quantity of said alkanecarboxylic acid in an acid saturator before entry into the reactor, wherein upstream of the acid saturator is connected a presaturator in which the cycle gas is loaded with another quantity of the alkanecarboxylic acid and then is transferred into the acid saturator, wherein the cycle gas enters the acid saturator from the presaturator as a main stream and as a substream introduced into the acid saturator as a bypass above the main stream.

6. The process according to claim 1, wherein a liquid comprising alkanecarboxylic acid is withdrawn from a bottom part of the acid saturator and is recycled into the acid saturator after heating.

7. The process according to claim 1, wherein the alkene is ethylene and the alkanecarboxylic acid is acetic acid.

\* \* \* \* \*